United States Patent [19]

Hofmann

[11] 4,226,590
[45] Oct. 7, 1980

[54] DEVICE IN DENTAL SUCTION APPARATUS FOR CONNECTING AND HOLDING SUCTION NOZZLE TUBES AND/OR FOR FILTERING

[75] Inventor: Hans-Joachim Hofmann, Geradstetten, Fed. Rep. of Germany

[73] Assignee: Dürr-Dental KG, Bietigheim, Fed. Rep. of Germany

[21] Appl. No.: 889,854

[22] Filed: Mar. 24, 1978

[30] Foreign Application Priority Data

Mar. 25, 1977 [DE] Fed. Rep. of Germany ....... 2713320

[51] Int. Cl.³ ............................................. A61C 19/02
[52] U.S. Cl. ....................................... 433/28; 433/98; 433/91; 433/97; 433/95
[58] Field of Search ........................... 32/22; 73/425.6; 261/44 C, 64 C

[56] References Cited

U.S. PATENT DOCUMENTS

| 3,445,934 | 5/1969 | Harris | 32/22 |
|---|---|---|---|
| 3,537,447 | 11/1970 | Gauthier et al. | 32/22 |
| 3,638,310 | 2/1972 | Austin, Jr. | 32/22 |
| 3,672,059 | 6/1972 | Booth | 32/22 |
| 3,847,573 | 11/1974 | Gandrad | 32/22 |
| 3,872,593 | 3/1975 | Thornton, Jr. et al. | 32/22 |
| 4,064,630 | 12/1977 | Killick | 32/22 |

*Primary Examiner*—Louis G. Mancene
*Assistant Examiner*—Michael J. Foycik, Jr.
*Attorney, Agent, or Firm*—Robert E. Burns; Emmanuel J. Lobato; Bruce L. Adams

[57] ABSTRACT

Dental suction apparatus is a modular construction, made up of a plurality of modules joined fluid-tight side-by side. A main suction duct extends through all of the modules. At least two of the modules have connection for suction hoses each having a suction nozzle, holders being provided on the modules for holding the suction nozzles when not in use. At least one module has a filter chamber connected between a suction tube and the main suction duct. A removable filter unit in the filter chamber has a basket-shaped filter on a stem by means of which the filter can be removed through on opening closed by a hinged cover. A cap on the stem provides a seal for the filter chamber. Flow of air from the suction tube of each suction tube module to the main suction duct is controlled by a valve in the form of a bellows provided with a telescopic guide and with a control valve for controlling the expansion and contraction of the bellows by differential pressure.

23 Claims, 10 Drawing Figures

DEVICE IN DENTAL SUCTION APPARATUS FOR CONNECTING AND HOLDING SUCTION NOZZLE TUBES AND/OR FOR FILTERING

The invention relates to devices in dental suction apparatus for connecting and holding suction tubes, and for shutting off, and optionally metering and/or filtering the suction air, having a casing and connections.

Such devices may be referred to as racks, because the connector devices or couplings at the ends of the suction nozzle tubes, for receiving the nozzles, mouthpieces, saliva removers, funnels or the like are releasably held at these devices. At the work station such devices are the central location from which suction air for the various dental treatments can be obtained. They are designed ergonomically and are arranged to be easily gripped by the dentist and/or the dental assistant. As a rule they have a connection for the suction tube which leads to the suction source. Moreover, when used as a rack, at least one connection for a suction nozzle tube is provided. Devices of this kind are known in which two suction nozzle tubes with holder means associated therewith and switching means for shutting off and in certain circumstances metering the suction air are combined to form a unit which comprises only one suction tube connection. The devices known heretofore do not do justice to all the frequently changing demands. On the one hand they cannot be enlarged. On the other hand the air valve cross-sections are small, and there exists the danger of depositions from the suction medium. Also suction noises occur at times, when the valves present in the racks do not close perfectly in suction installations which supply a plurality of treatment spaces. Also the known filter devices in suction installations are not completely satisfactory from the point of view of servicing and hygiene.

An object of the invention is to improve devices of the kind referred to above, in a plurality of respects, above all in relation to the hygienic conditions, the facilities for varying the configuration of the work station in accordance with the wishes and needs of the dentist, and in respect to maintenance.

According to a first aspect of the invention a device in dental suction apparatus for connecting and releasably holding at least two suction nozzle tubes, for shutting off, and optionally metering and/or filtering of the suction air, with a casing provided with connections for the suction pipes and/or suction ducts leading to movable suction nozzle tubes, a shut-off member for each suction nozzle tube, and control means for the actuation of the shut-off members, is characterised in that for each movable suction nozzle tube and/or suction pipe connection a respective module is provided which is fitted with connector and adaptor means for selective connection with further modules and which comprises at least one duct which extends through the module and which, together with the duct or ducts of further modules forms a common main suction duct leading to a suction pipe connection module; optionally the module includes at least one control duct. Whereas the devices known heretofore either were constructed solely for connecting a suction tube to appropriately fitted valves and holder devices, or comprised at most two suction tubes in a fixed arrangement on both sides of a central suction return tube, the invention renders it possible to group together two, three or even more suction nozzle tubes for various purposes and/or of different size in one rack and also to dispose them relative to each other and to the suction pipe module in any desired manner. There is no need to construct, offer for sale and stock special complete devices for each individual case, because different assemblies can be built up now from the individual modules in accordance with requirements. Thereby production and stock keeping can be simplified and rendered more economical to a considerable extent. They also offer advantages in respect of servicing technique. There is no compelling need for combining the individual modules to form a respective complete rack, but they may even be inserted with their individual component parts in otherwise differently constructed work units of the dentist and may be combined with other suction apparatus elements, even from different manufacturers.

For hygienic and practical reasons, good filtering of the suction medium is necessary in dental suction apparatus. Heretofore the filters were disposed at various locations, dependent upon the design. In particular pre-filters are often unfavourably located. However, when valuable pieces of filling, parts of prosthesis, or the like are sucked away unintentionally, the dentist must be able to remove these from the suction apparatus. The invention now offers a favourable possibility, namely in that the filter, which is accessible under a closure, is arranged in the construction unit which receives the connecting elements of the suction nozzle tubes. Thus the filter is provided in the immediate vicinity of the work station of the dentist, and articles to be recovered may be very easily removed from there. They must be located either in the filter or in the suction tube portion leading up to the filter. Since this path is short, the articles being looked for can be found quickly. In this case it is not essential that the device is assembled from individual modules which are selectively combinable with other modules. Such a filter may alternatively be arranged in a complete unit for a defined number of suction tubes in the manner according to the invention. The essential features of such a device as described below.

The previous filters in dental suction apparatus are not fully satisfactory in a hygienic respect. The invention provides a considerable improvement even for this, in that the filter is associated with a hand grip disposed (in use) outside the suction medium stream, and an ejector. The soiled filter, to which many bacteria adhere, can be removed from its casing by means of the handgrip and be ejected into a waste container by means of the ejector without the soiled filter being touched. This measure, too, is not absolutely limited to devices built up from modules which are constructed in a defined manner, or not even to the fact that the filter is arranged in the immediate vicinity of the suction nozzle tubes. On the contrary, a filter fitted with handgrip and ejector may be arranged even in existing suction apparatus or in apparatus of different construction at any desired location, although it is particularly favourable to accommodate it in apparatus with modules and close unification of filter and connecting element and valves. The features required for such an ejector filter are described below. Such a filter may be arranged optimally with advantage at the central terminal location, that is to say at the earliest possible point at a central location of the device where a plurality of suction nozzle tubes are brought together.

The construction of the filter, its handgrip and the ejector may be effected in many ways. An advantageous embodiment of the invention provides the handgrip of the filter in the form of a cap with a grip profile, the actuator element of the ejector lying in the grip region thereof. Thus the filter element with its cap can be gripped with two fingers and easily actuated in the immediate vicinity of the ejector. For this purpose the ejector may be formed by a plunger rod the upper end of which extends through the removable cap which is sealingly arranged in the casing. On the one hand such a construction is particularly simple to produce and may be well formed by throw-away parts, so that also the plunger rod which comes into contact with the bacteria is always destroyed at the same time. Such a solution has the further advantage that in the absence of a filter and/or the ejector rod, that is to say when at least one of the parts is not present as it should be, the suction air stream sucks in air through the outlet opening for the plunger rod end, whereby a whistling noise is produced which indicates to the operator immediately upon switching on of the suction apparatus that the correct filter insert is absent.

In order to avoid special holder elements, the plunger rod may be retained in the cap bore in a clamping manner. For this purpose abutment beads and detent grooves on the plunger rod may co-operate with abutment and detent beads in the region of the cap bore. Thus there results in a simple manner a construction which satisfactorily transmits retaining forces, but which is easily releasable and can be satisfactorily produced by a synthetic resin moulding method.

The invention may advantageously provide a construction of the filter such that the filter body adheres to the ejector rod, and cap and filter body are located on respective sides of a suction stream inlet opening and are appropriately sealed. In order that it is possible to see from the outside of the filter casing whether the filter is properly inserted, it is advantageous to arrange a portion of the ejector device to terminate in a bore of the casing visible to the user.

The invention in a further aspect provides a device apparatus for connecting and releasably holding suction tubes, shutting off and optionally metering the suction air, with a pneumatic valve disposed in a casing and a closure for the suction pipe leading to the suction source, at least one suction nozzle connection, at least one closure element free of sliding seal surfaces and closing in the flow direction, and underpressure control means, with the improvement that the closure element is a corrugated bellows provided with a sealing lip. Whereas heretofore diaphragm seals clamped in the region of the suction medium stream were regarded as optimum solutions, the corrugated bellows offers, for a small constructional size of the total arrangement, a large opening stroke and, above all, casing faces in the region of the seat which are free of corners and edges at which bacteria and other constituents of the suction medium might settle. It permits many more variation possibilities in the configuration of the individual valve and/or module elements.

The displacement of the closure element may be effected for example in the horizontal direction. However, when the suction duct comprises a vertical suction duct region, the opening or closing movement, respectively, of the closure element is assisted by the inherent weight of the movable part of the corrugated bellows. The sealing lips of the corrugated bellows can seal the rim of a suction duct bore during closing. However, particularly favourable sealing conditions are obtained when a sealing seat is provided which narrows conically downwardly and which has a circular cross-section, like the corrugated bellows and the sealing lip. When the sealing seat face is connected to a section of a diverting duct, a compact construction may be realised in which the suction nozzle connections can be provided from below with a suction nozzle tube. It is also avoided thereby that the suction nozzle tube is additionally bent in the region of the connection.

For a satisfactory suction effect at the suction nozzles it is important that the pressure losses due to wall friction and other factors influencing the suction medium flow are kept as small as possible. For this purpose it is provided that all ducts provided in the casing have smooth wall surfaces and the diverting section optionally comprises guide profiles which guide the suction medium stream past the lower end of the open closure element, whereby also the deposition of secretion constituents is prevented or reduced.

The control of the pneumatic closure element may be effected in many ways. Thus for example external control tubes and further control means may be provided. However, it is particularly advantageous, for a closed compact manner of construction, if a control duct is arranged parallel to the suction duct and is connected to the control chamber of the closure element. The control of the pneumatic closure element may then be realized in a particularly effective and problem-free manner when the control duct is associated with a suction nozzle arrangement which draws air from the surroundings to the control duct through a by-pass suction tube, a nozzle bore, a suction gap, a suction bore and a bellows control duct, and thereby effects an underpressure amplification. It is constructionally simple and advantageous in this case if the suction gap of the suction nozzle arrangement is formed between the bottom of a bellows control ante-chamber and the lower end of the by-pass suction tube. Since the full difference pressure between the ambient atmosphere and the suction pressure at the suction unit end prevails at the suction gap, a strong suction effect is produced in the suction gap of the suction nozzle arrangement (Borda nozzle) and creates in the bellows control chamber an underpressure which is greater than in the main suction duct and which is sufficient, without external energy, for opening the closure element fully.

For the closure of the closure element, a venting device for the bellows control chamber may be arranged which is switched for example manually or electrically. However, it is particularly advantageous to provide a venting switch which is actuated by a switch actuator flap or the like upon insertion of the suction nozzle tube, since then the closure element is automatically closed in a smell-sealing manner when the suction nozzle tube is not being used.

For ease of assembly and under certain circumstances servicing, as well as for the arrangement as a compact small module, each module may consist of three casing parts which are disposed one on top of another in a sealing manner and one of which comprises a horizontally located main suction duct and a vertical connecting duct. If the tube connection, the main suction duct, the sealing seat and the suction nozzle connection are arranged in the lower casing part, the diverting section and the venting switch in the middle casing part, and the guide means for the closure element in the upper casing part of the suction nozzle tube module, particularly short duct ways are present and the suction tube may be arranged to hang in a manner convenient for working. Since the closure element is formed by a corrugated bellows which may have a long opening stroke, this corrugated bellows may be clamped particularly advantageously between the middle and the upper casing part and may be provided with a corrugated bellows control chamber in the upper casing, since then the upper casing part may be particularly small.

Since the closure element closes in the flow direction of the suction stream, a good shut-off is obtained. Since the suction stream impinges laterally on the closure element, additional guide means for perfect guidance of the closure element may be provided which for example guide the closure element from outside. However, additional friction is produced thereby at the closure element and may lead to wear. If the guide means are provided in the interior of the closure element, and are constructed for example as a telescopic guide with extension limiters, a low-friction guidance for the closure element can be realised.

Further important features of the invention, details, embodiments and advantages of the invention are dealt with in the following description relating to the drawings.

One constructional example of the device according to the invention is illustrated in the accompanying drawings, in which FIG. 1 is an oblique side view of a device according to the invention, wherein only one inserted suction tube is shown, the lower portion thereof as well as the lower half of the filter module not being shown;

The illustrated constructional example of a device in dental suction apparatus is provided for an arrangement between suction nozzle and suction aggregate, in order to render possible a connection and retention of any desirable number of suction nozzle tubes of under certain circumstances different sizes which are supplied with suction pressure by a single suction tube leading to a suction aggregate. The mixture of suction air and water, blood, blood foam, saliva, tooth substance and the like is sucked in through suction nozzles which are inserted in the suction nozzle tubes. Furthermore, measures for shutting off, metering and filtering the suction air are provided in the device and are explained below with reference to the Figures.

Figure 1:
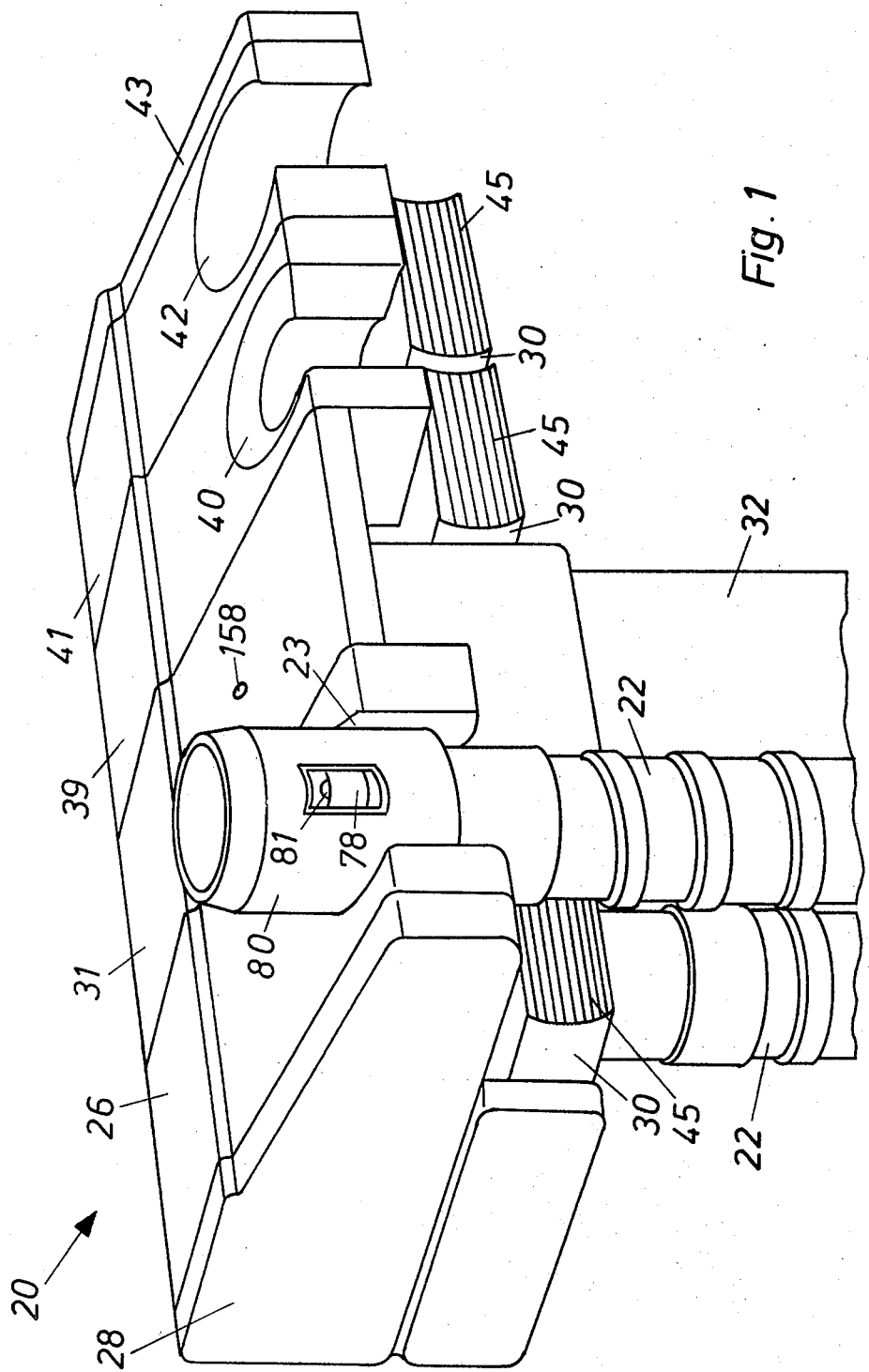

FIG. 1 is an oblique side view of a device 20 which is assembled from four individual modules 26, 31, 39 and 41. For simplification, only one connected suction nozzle tube 22 is illustrated, with its free end hung from a fork-shaped suspension holder 23 of the left-hand suction module 26, to which the tube is connected. The left side of the suction module 26 is closed by a cover plate 28 the contour of which is matched to that of the suction module 26. There follows, on the right-hand side of the suction module 26, a filter module 31 of substantially the same external contours which, however, unlike the suction module 26, extends downwardly into a cylindrical portion 32 which, as may be seen from FIG. 6, terminates at its lower end in a coupling tube member 34 to which is attached by means of a quick-coupling device 35 a suction tube 37 which leads to a suction unit (not illustrated). On the right, adjacent to the filter module 31, there is a suction module 39 the fork-shaped holder 40 of which is provided for a suction nozzle tube with a smaller diameter than tube 22. Adjoining the module 39 is a suction module 41, with like contours, identical to the suction module 26, with a tube holder 42. The right-hand side of the suction module 41 is provided with a cover plate 43 which, as to its connecting contours, is matched to the abutment face of the suction module 41. Below the fork-shaped holders 23, 40, 42, the suction modules 26, 39 and 41 have similar locking buttons 30 which are offset backwards approximately by the order of magnitude of the tube diameter. All edges of the device 20 which lie in the operating region are rounded, and the bounding casing surfaces are smooth-faced, except for the profiling 45 of the buttons 30. The side faces of the modules, at which the modules are connected to one another, are of the order of size of the palm of a hand, their width amounts to approximately 3-5 cm. The cylindrical portion 32 of the filter module 31 has a length of approximately 10 cm.

Figure 2:
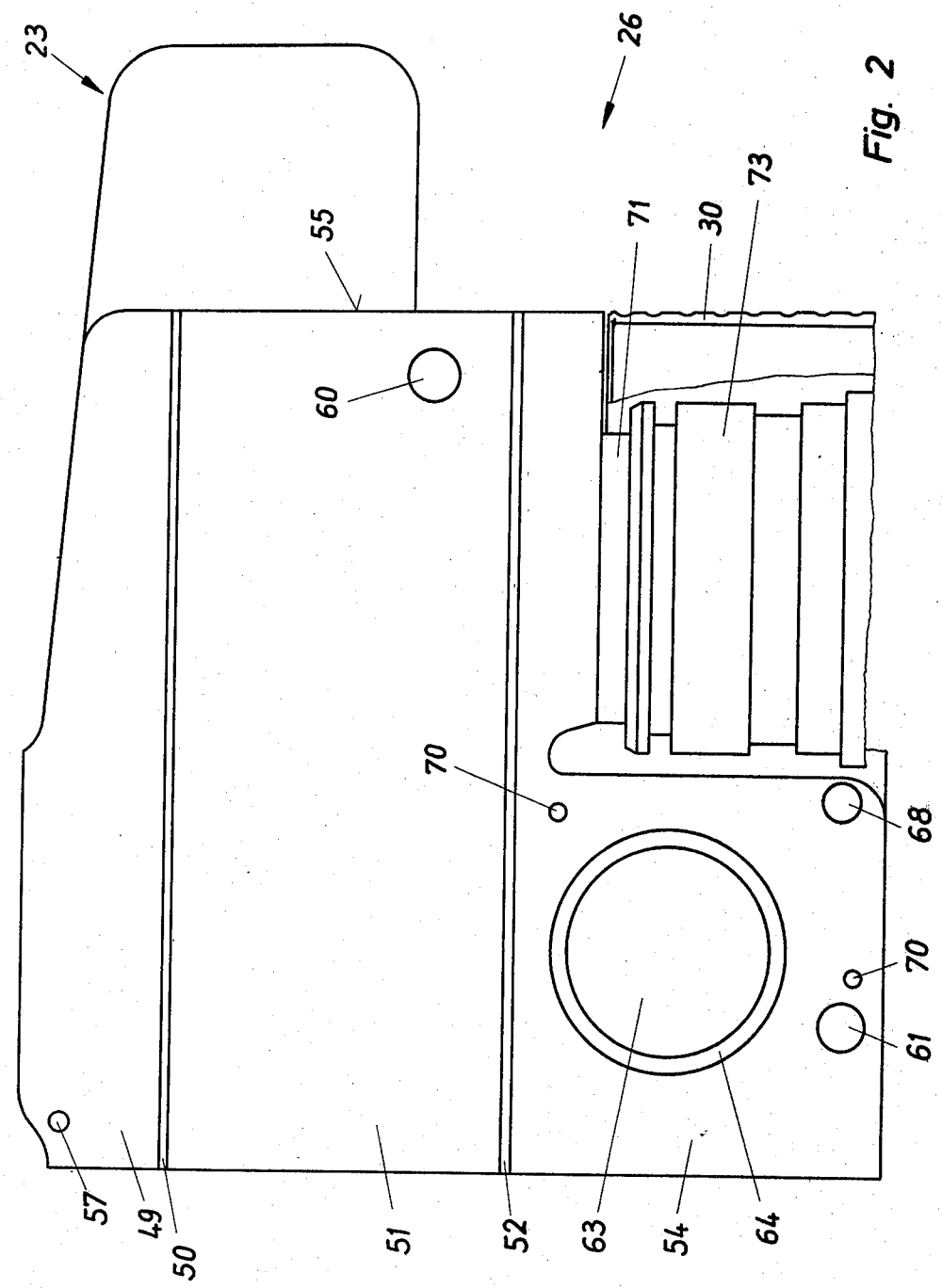
FIG. 2 is an end view, from the left, of a constructional example of a suction module.
Figure 3:
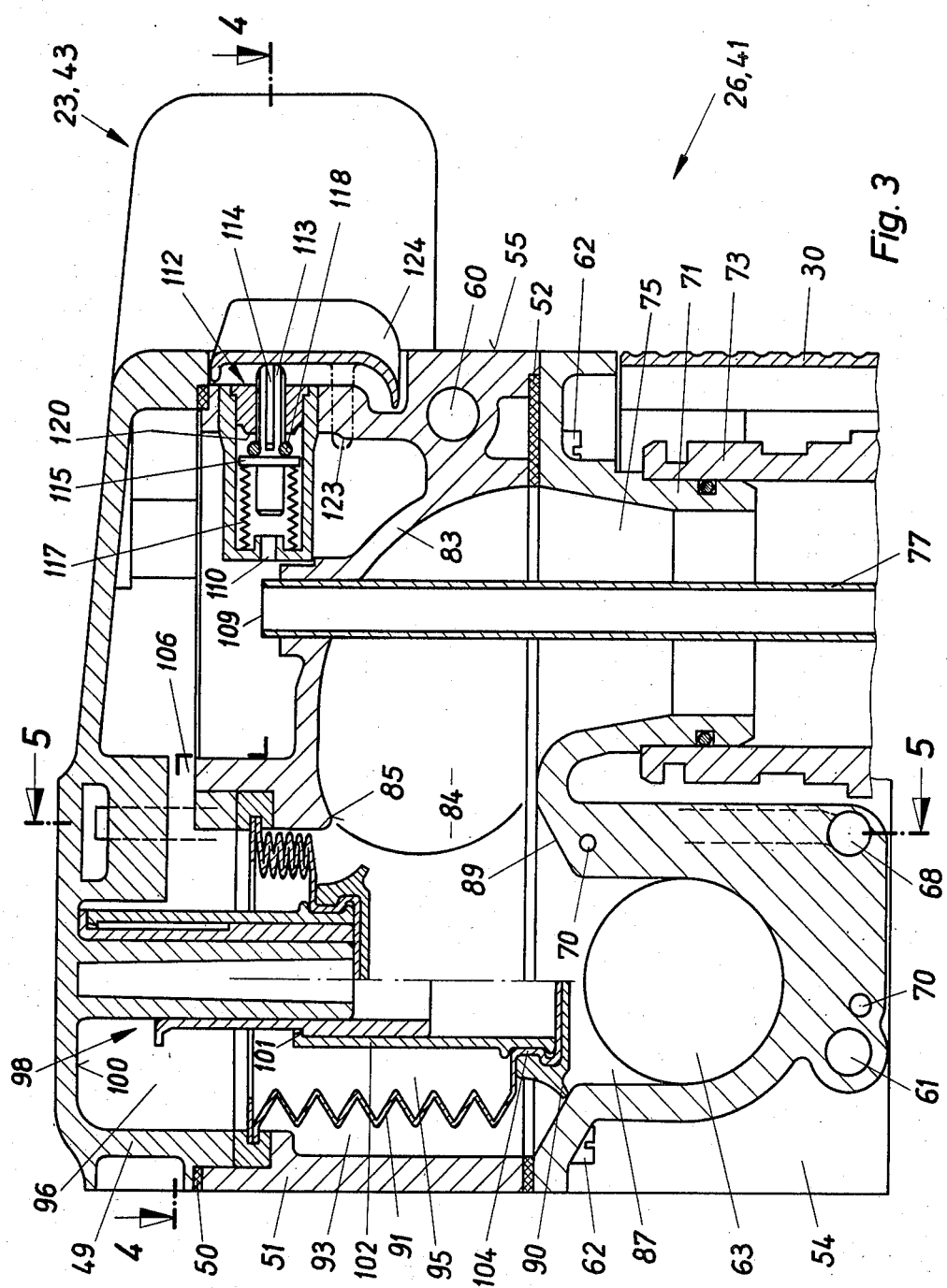
FIG. 3 is a vertical section on the line 3—3 in FIGS. 4 and 5, through the suction module according to FIG. 2.
Figure 4:
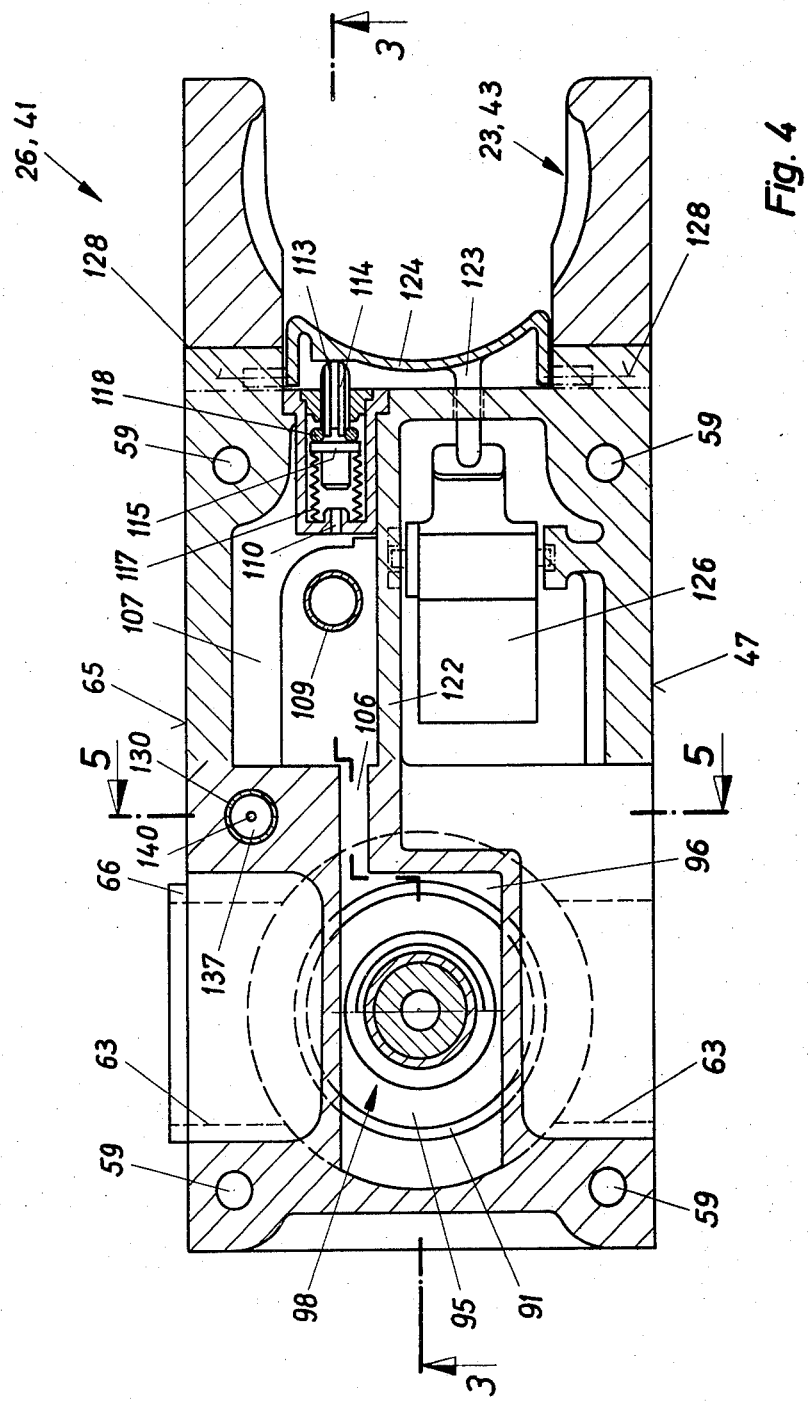
FIG. 4 is a horizontal section on the line 4—4 through the suction module according to FIG. 3.

FIG. 2 is a side view showing the connecting face 47 of the suction module 26, with the cover plate 28 removed. The casing of module 26, which consists of a synthetic resin, as in all the modules, is assembled from an upper part 49, a middle part 51 and a lower part 54. The three casing parts, as may be seen from FIG. 3, are vertically screwed together by means of assembly screws 62, with intervening seals 50 and 52. The holder 23 is formed on the upper casing part 49, projects beyond the width of the middle casing part 51 and the lower casing part 54, and extends along the edge 55 downwardly past the centre of the middle casing part 51. The upper casing part 49 has in the left-hand upper corner (in FIG. 2) a hinge hole 57 which is provided for mounting a cover 58 of the filter module 31. The middle casing part 51, which in the side view according to FIG. 2, is rectangular, comprises in the region of the right-hand lower corner a horizontal assembly bore 60 which extends through the entire casing. The left-hand half of the lower casing part 54 is approximately square in side view. Approximately in the centre of the square, a main suction duct 63 extends horizontally and rectilinearly through the entire casing. The mouth of the main suction duct 63 shown in FIG. 2 is provided with an annular groove-like enlargement 64 in which, for the purpose of accurately fitting assembly of two adjacent modules, a flange 66 can engage, which flange is formed around the mouth of the main suction duct 63 on the opposite connecting face 65 as shown in FIG. 4. Below the main suction duct 63, a control duct 68 is provided which extends parallel thereto.

Furthermore the left-hand lower casing part 54 comprises an assembly bore 61 which extends horizontally through the entire casing, as well as two smaller holes 70 for fixing the cover plate 28. The right-hand part of the lower casing 54 is formed by a connecting tube member 71, to which the suction nozzle tube 22 is connected by means of a quick-coupling device 73 and is locked by means of the button 30.

FIG. 3 illustrates a vertical section through the suction module 26 or 41, which differs from the suction module 39 merely by the size of the tube holder, and the additional control pipe 77. Above the connecting tube member 71, there is a vertical suction duct 75 which widens approximately conically as far as the casing seal 52. The suction duct 75 contains the additional control pipe 77, which leads through an auxiliary control tube (not shown) arranged in the suction nozzle tube 22, to a restrictor slider 78 at the nozzle end of the tube 22 in the region of a holder 80 for the suction nozzle (see FIG. 1). The suction effect available at the suction nozzle can be controlled by displacing the restrictor slider 78 over a control opening 81, as will be explained below.

Above the casing seal 52, the suction duct 75 communicates smoothly with a diverting section 83 which diverts the suction stream in the direction of the main suction duct 63. The upper edge of the horizontal intermediate region 84 is provided with a profiled edge 85 which guides the suction stream to the main suction duct. A further vertical suction duct region 87 parallel to the suction duct 75 terminates in the main suction duct 63; it comprises, facing the casing seal 52, a horizontal dished annular sealing seat 89 on which a sealing lip 90 of a closure element 91 can engage for sealing abutment. The closure element 91 is constructed without sliding sealing surfaces, being a corrugated bellows, and is movable in a vertical direction above the vertical suction duct 87 in a chamber 93 which follows the horizontal intermediate region 84 and has a circular cross-section. The bellows 91 and the sealing lip 90 have circular cross-sections. The interior space 95 of the bellows 91 is open upwardly to a bellows control chamber 96 which is formed in the upper casing part 49 of the suction module 26 or 41. The upper wall 100 of the bellows control chamber 96 has a vertically downwardly directed telescopic guide 98 attached thereto which consists of three coaxial longitudinally slotted tubes which are provided with stops 101 and the outermost tube 102 of which is connected, in the region of the sealing lip 90, to the bellows 91 by means of a bead 104 formed in the latter. The telescopic guide 98 has no sliding sealing faces. It permits perfect vertical guidance of the bellows 91 from the lowermost closure position of the bellows through a large opening stroke to the uppermost open position, without the flow forces of the suction medium pressing the bellows out of its vertical direction of movement.

The bellows control chamber 96 is connected to a bellows control ante-chamber 107 by a connecting duct 106. The bellows control ante-chamber 107 is formed in the right-hand part (as seen in FIGS. 3 and 4) of the upper casing part 49 and in the right-hand upper part of the middle casing part 51 between the bellows control chamber 96 and the holder 23 or 43, as may be seen from FIGS. 3 and 4. The end 109 of the additional control pipe 77 projects into the bellows control ante-chamber 107. Furthermore, when the suction nozzle tube 22 is hung in the holder, a connection from the chamber 107 to the ambient atmosphere exists through an inlet bore 110 of a suction-tube-sensing switch 112 by way of grooves 113 in a plunger 114 when the button 30 is pressed in by the nozzle holder 80, whereby a plunger plate 115 formed on the plunger 114 together with its ring seal 118 is lifted off a sealing seat 120 against the effect of a closing spring 117. Beside the plunger 114, on the other side of a separating wall 122, a switch plunger 123 is formed on a switch actuator flap 124 and actuates an electrical switch 126 in such a manner that after removal of the suction tube 22 from the holder 23, the switch actuator flap 124 is rotated about a pivot axis 128 under the effect of the closing spring 117, which causes closure of the switch 126 and in consequence thereof switching on of the suction unit. All the electrical switches 126 arranged in the individual suction modules are connected in parallel, so that the suction unit is not switched off until the last suction nozzle tube has been hung again in its holder 23, 40 or 42.

Figure 5:
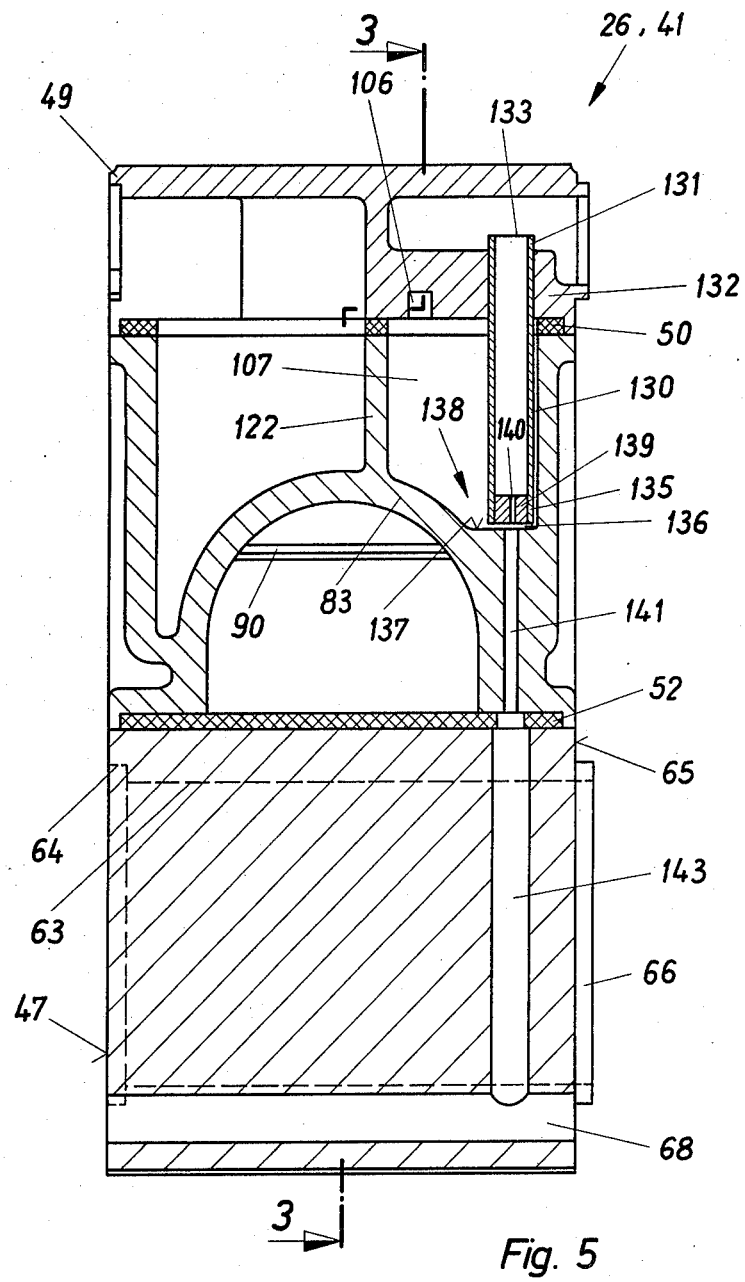
FIG. 5 is a vertical section on the lines 5—5 in FIGS. 3 and 4.

As may be seen from FIG. 5, a by-pass suction tube 130 projects into the bellows control ante-chamber 107; its upper half 131 is inserted into a casing formation 132 of the upper casing part 49 which partly closes the bellows control ante-chamber 107 upwardly laterally of the separating wall 122. The mouth 133 of the by-pass suction tube 130 has a connection to the ambient atmosphere. The lower end 135 of the by-pass suction tube 130 extends so far towards the bottom part 137 of the bellows control ante-chamber 107 that only a narrow suction gap 136 remains. A plug 139 with a nozzle bore 140 is inserted in the lower end 135. Opposite the outlet opening of the nozzle bore 140, the bottom portion 137 of the bellows control ante-chamber 107 has a suction bore 141 provided therein the diameter of which is approximately three times as large as that of the nozzle bore 140. The suction bore 141 extends as far as the casing seal 52 and terminates there in a vertically extending bellows control duct 143 the diameter of which is approximately three times as large as that of the suction bore 141. The bellows control duct 143 terminates in the horizontally disposed control duct 68. The suction nozzle arrangement 138 (Borda nozzle) formed by the by-pass suction tube 130 with the nozzle bore 140 by way of the suction gap 136 and the suction bore 141 serves for producing in the bellows control ante-chamber 107 an underpressure which is required for the opening of the closure element 91.

Figure 6:
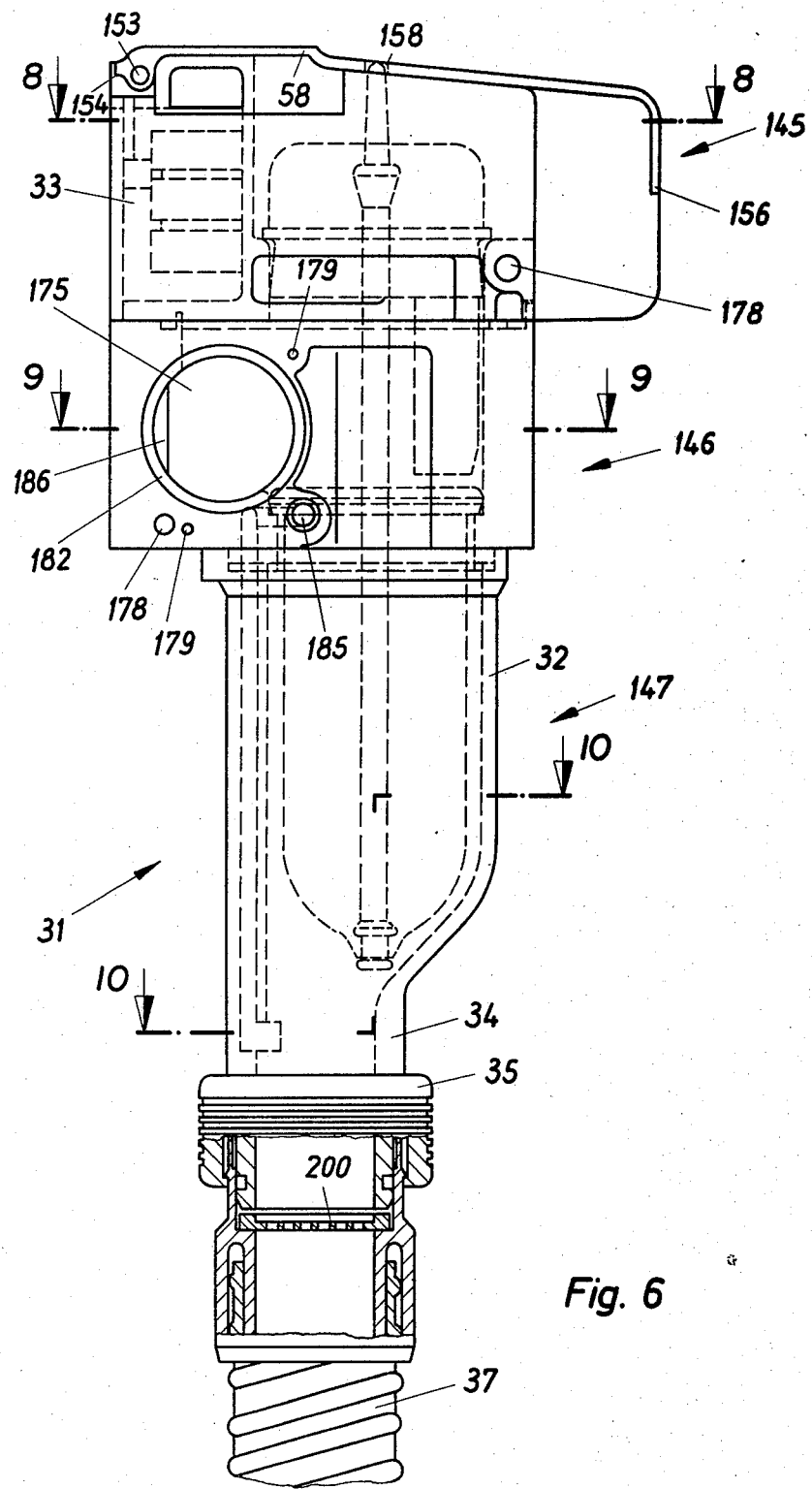
FIG. 6 is an end view from the left of a constructional example of a filter module, with a partial section of the connection of the suction tube.
Figure 7:
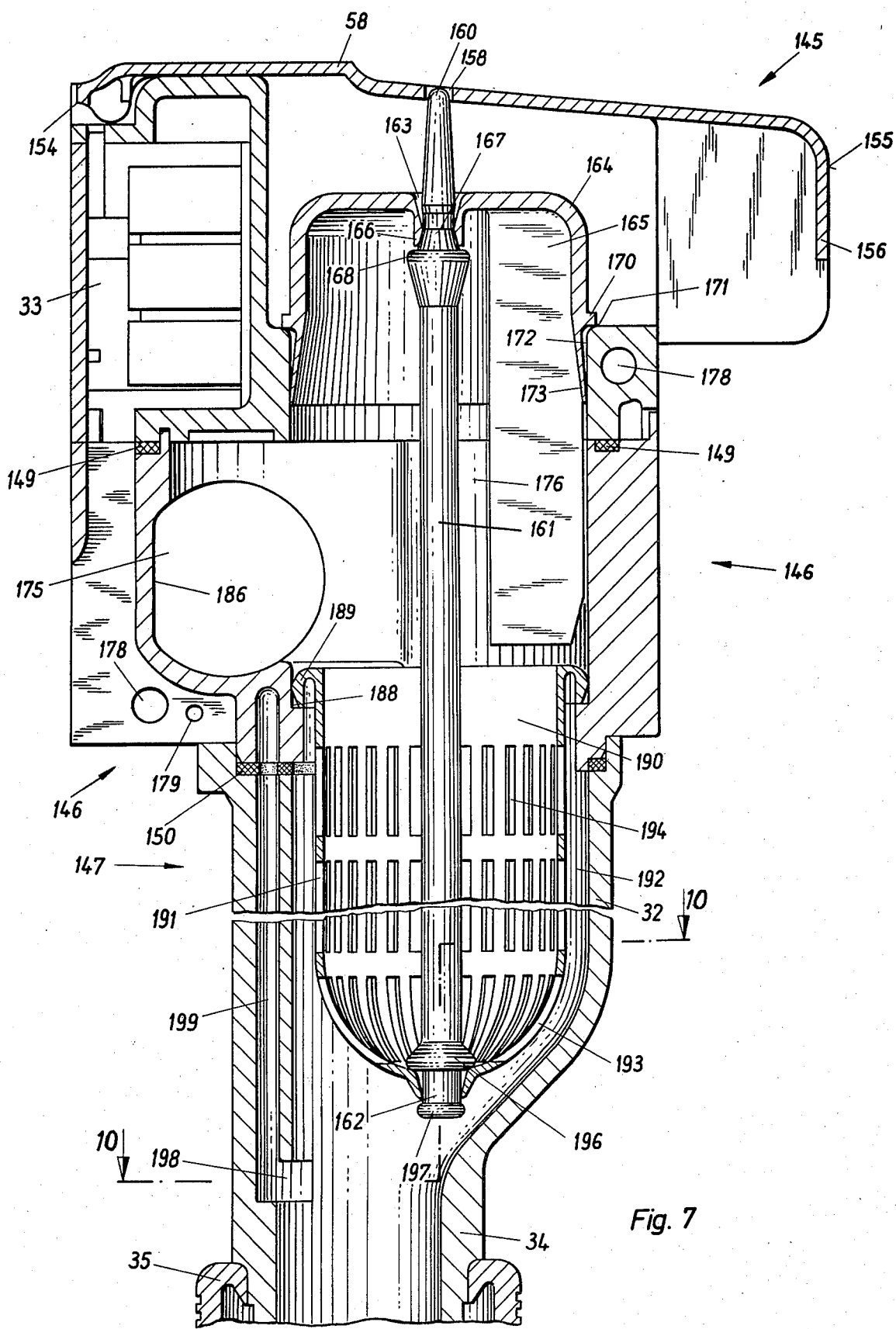
FIG. 7 is a central vertical section on an enlarged scale on the line 7—7 in FIG. 8 through the filter module according to FIG. 6.
Figure 8:
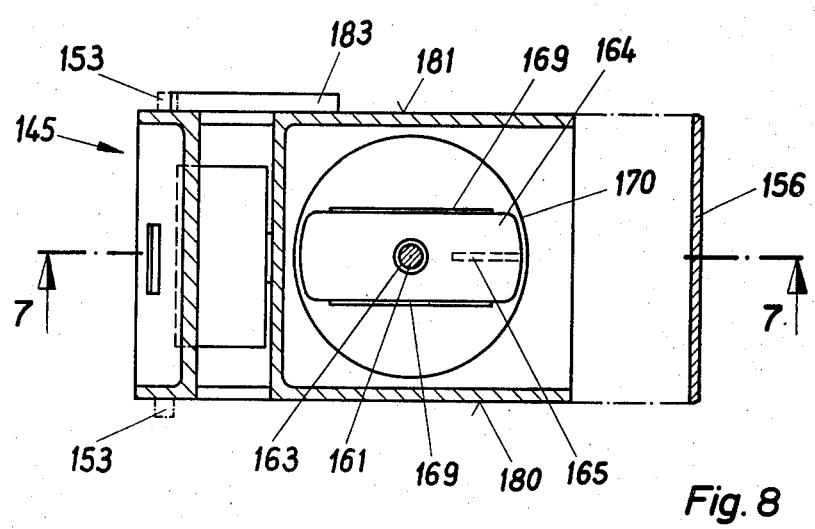
FIG. 8 is a horizontal section on the line 8—8 through the filter module according to FIG. 6.
Figure 9:
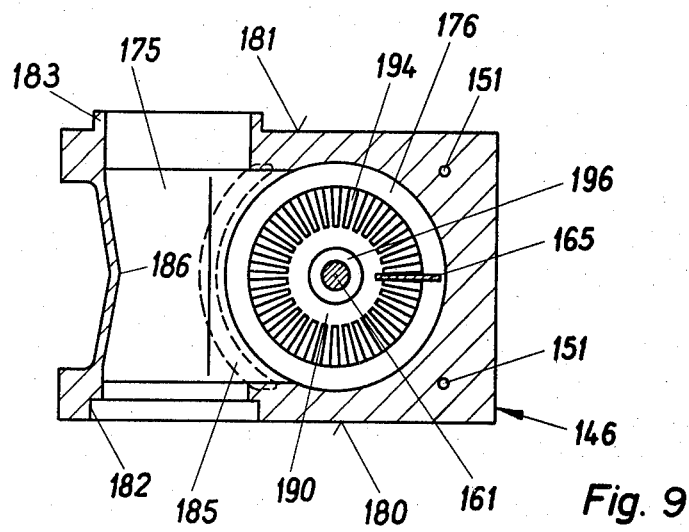
FIG. 9 is a horizontal section on the line 9—9 through the filter module according to FIG. 6.
Figure 10:
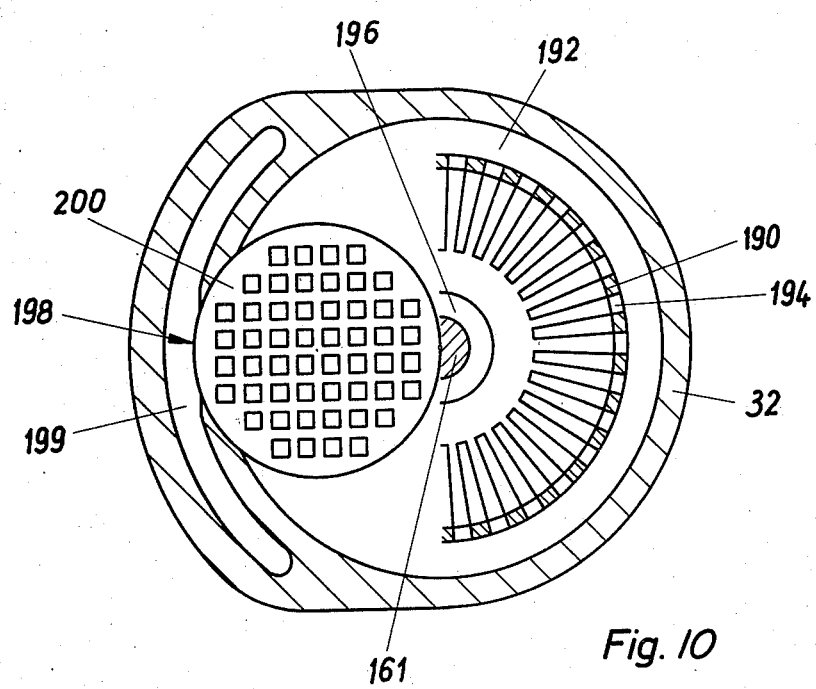
FIG. 10 is a horizontal section on an enlarged scale on the line 10—10 through the filter module according to FIG. 6 and FIG. 7.

FIG. 6 is a view from the left of the connecting face of a filter module 31. FIG. 7 illustrates an enlarged central vertical section through the upper casing part 145, the middle part 146 and the lower casing part 147 of the filter module 31. The horizontal sections in FIGS. 8 and 9 correspond, as to the order of magnitude, to FIG. 6, whereas the horizontal section in FIG. 10 is on a larger scale. The upper part 145 and the middle part 146 are sealingly connected by means of a casing seal 149. A casing seal 150 is located between the middle part 146 and the lower part 147, and the three casing parts are vertically screwed together by way of the bore 151. The upper casing part 145 is closed by a cover 58 which, during the assembly of the filter module 31, is retained by means of cover studs 153 arranged on both sides, either in the mounting bores 57 of the adjacent suction modules or in appropriately provided mounting bores in the cover plates 28, 43. Behind the cover stud 153, the cover 58 has an abutment 154 formed thereon which permits the cover to be swung open to just beyond the vertical position. Following the lateral/contour of the suction modules, the cover 58 comprises an incline in the direction of its front edge 155 and terminates in a vertical portion 156 which finishes approximately in the centre of the upper casing part 145. For opening the cover 58, the vertical portion 156 is gripped from behind. Furthermore, the cover 58 comprises, approximately in the centre of the cover, a bore 158 into which projects the end 160 of an ejector plunger rod 161. The rod end 160 is conically enlarged downwardly and is located in a bore 163 of a handgrip cap 164. An abutment and detent bead 166 which faces downwards in the region of the bore 163 is formed on the cap 164 and engages in an annular detent groove 167 in the plunger rod. Below the groove 167 the plunger rod 161 has an abutment bead 168. The cap 164 is formed with a hatshaped profile and is provided laterally with grip profiles 169 which are indicated in FIG. 8. An external abutment ring 170 is located at the lower end of the cap 164; it lies on a surface 171 of the upper casing part 145 and is downwardly conically enlarged to form sealing lips 173 which seal in the region 172 of the upper casing part 145. The cap 164 is thereby separated from the filter ante-chamber 176, into which enters the suction medium from a main suction duct 175.

Like the lower casing part 54 of the suction module 26, 39 or 41, the middle casing part 146 of the filter module 31 comprises a main suction duct 175 which extends horizontally through the casing, as well as corresponding assembly bores 178 and 179. The duct 175 is provided on the left-hand (as seen in FIG. 1) connecting face 180 with a circular groove-shaped enlargement 182 and on the right-hand connecting face 181 with a matching flange 183 in order to permit the filter module 31 to be connected to the suction modules 26, 39 and 41, in a correctly fitting manner. For this purpose, the control duct 185, which is arcuate in the interior of the casing, also extends to the left-hand and right-hand connecting faces 180, 181 of the casing part 146. The middle region of the main suction duct 175 comprises a vertical restriction 186 which exerts a deflecting effect on the suction medium currents which enter the main suction duct 175 from both ends. In order to avoid additional eddy losses in the filter ante-chamber 176, a central separator blade 165 projects into the latter vertically in its front portion; the blade is formed on the cap 164. Below the blade 165 an annular groove step forming a sealing seat 188 is provided in the casing part 146 for sealingly receiving the sealing bead 189 provided on the filter body 190. By means of the sealing bead 189 the filter ante-chamber 176 is hermetically closed from filter chamber 192. The filter chamber 192 receives a filter body 190 into which the plunger rod 161 is symmetrically inserted. The filter body 190 consists of a cylindrical section 191 and a bowl-shaped lower terminal cap 193, both with rectangular outlet openings 194. The lower end of the terminal cap 193 is provided with a bead-like detent device 195 in which the lower and 162 of the plunger rod 161 is held by means of appropriately formed abutment and detent beads 196, 197 thereon. The region of the space provided under the terminal cap 193 for the coupling tube 34 has arranged therein a control suction opening 198 which opens into a sickle-shaped main control duct 199 which is separated from the filter chamber 192 and terminates at its top in the control duct 185. Through this control suction opening 198 and the main suction duct 199 as well as the control ducts 185 and 68, respectively, an underpressure is available at the suction nozzle arrangement 138 which is not weakened by the throttling effect of the filter body 190. Below the quick coupling device 35, a tube filter 200 is disposed in the entry region of the suction tube 37 and functions as an additional filter. In the rear region of the upper casing half 145, a space 33 is provided which provides room for additional switches may be needed in certain circumstances, and for mounting means for attachment in the treatment region.

The whole apparatus operates in the following manner:

In the rest state, i.e., when no suction power is required at any suction nozzle tube 22, the suction unit is switched off and the nozzle holders 80 at the ends of the tubes 22 are hung in the fork-shaped holders 23, 40, 42 in such a manner that the respective switches 112 assume the position illustrated in FIG. 3. Air at atmospheric pressure can then enter by way of the grooves 113 of the plunger 114, past the ring seal 118, through the inlet bore 110 into the bellows control ante-chamber 107. This atmospheric pressure is transmitted through the connecting duct 106 to the bellows control chamber 96, and the bellows 91 closes the sealing lip 90 onto the sealing seat 89 owing to the resilience of the bellows and its own weight, since atmospheric pressure prevails also in the main suction duct 63. Thereby an efficient closure of the main suction duct 63 against odours is obtained, when either the entire installation is out of operation or the tube 22 is suspended from the holder 23. The closing movement of the bellows 91 is aided by the suction effect in the main suction duct 63, when the suction tube of another suction module is not hung up and the suction unit is still operative.

When one or more suction tubes is removed from the holder, the switch actuator flap 124 pivots under the effect of its spring 177, about the pivot axis 128, whereby the plunger plate 115 with the ring seal 118 comes into sealing abutment on the sealing seat 120 and interrupts the access of atmosphere to the bellows control ante-chamber 107. Simultaneously the contacts of the electrical switch 126 are closed, whereby the suction unit is switched on.

The suction unit then produces through the suction tube 37, the coupling tube 34, the filter body 190 and the filter ante-chamber 176 a suction pressure in the main suction duct 175, which suction is transmitted to the main suction ducts 63 of the individual suction modules. At the same time an unrestricted suction pressure is produced through the control suction opening 198 which is arranged in the region of the coupling tube 34, through the main control duct 199 and the control duct 185; this suction pressure is likewise effective in the control ducts 68 of the suction modules and has a connection with the respective suction nozzle arrangements 138 in the individual suction modules. Since, in the suction modules in which the suction nozzle tube is still hung in the holder, the quantity of air which enters through the plunger 114 and the inlet bore 110 is greater than the quantity of air sucked away in the suction gap 136 of the suction nozzle arrangement 138, the closure element 91 remains closed in these suction modules. In the suction module in which the suction nozzle tube 22 has been removed from the holder 23, a strong suction effect is produced at the suction gap, since the full difference of pressure between atmosphere and suction pressure at the suction unit prevails at the suction nozzle arrangement 138, and leads to the effect that a larger underpressure is produced in the bellows control ante-chamber than in the main suction duct 63. This has the consequence that the bellows 91 contracts and opens the full flow cross-section available for the suction medium.

The suction power available at the suction nozzle of the suction nozzle tube can be controlled by means of the throttle slider 78 provided at the nozzle holder 80, through a pipe line and the additional control pipe 77 owing to the fact that the underpressure prevailing in the bellows control ante-chamber 107 is reduced by the entry of air from the atmosphere which is metered in accordance with the position of the throttle slider, this casing a lowering of the bellows 91 to the position in which a force equilibrium is established between the forces effective vertically at the closure element 90 of the bellows.

The filter body 190 which is aranged in the filter module 31 and which is provided for separating out larger solid substances, is mounted, for easy accessibility, in the region of the suction modules and can be interchanged in a simple and hygienic manner. For this purpose the cover 58 of the filter module 31 must be swung open. The handgrip cap 164 with the ejector plunger 161 is then accessible and can be removed upwardly together with the filter body 190, since the filter body 190 is inserted in the casing of the filter module without additional holding devices. The person removing the filter simply grips the cap 164 and pulls the filter body 190 together with the rod 161 upwardly out of the casing, without thereby coming into contact with the bacteria-containing filter region. By pressure on the tip 160 of the rod, the filter body 190 together with the rod 161 can then be removed from the cap 164 in a hygienic manner over a waste container. A further advantage of the filter construction according to the invention is that the filter body comprises only a direct seal 189 against the casing part 146 at the sealing seat 188 which seal, when the filter body 190 is pulled out, removes thr deposits which have collected at the sealing seat 188, in an upward direction. By the insertion of a fresh filter body 190 and a new rod 161, filter replacement is rapidly performed, and the whole suction installation can be brought into operation again after insertion of the filter body and the handgrip cap in the respective sealing seats 188 and 172. If the insertion of a fresh filter body 190 has been omitted, the absence of the filter makes itself noticeable by a whistling sound which is produced in the region of the cap bore 163. The absence of a filter body 190 and associated rod 161 can also be detected from the outside when the cover 58 is closed, by the fact that the rod end 160 does not project into the bore 158 provided in the cover 58.

What is claimed is:

1. Dental suction apparatus comprising a plurality of modules assembled side-by-side to constitute an assembly, each of said modules having a suction duct extending from one side to the other and connecting with the suction duct of at least one other module to constitute a main suction duct connected to suction producing means, each of at least two of said modules having means for attachment of a suction nozzle tube and with duct means connecting said suction nozzle tube with said main suction duct, and further having means for removably holding a suction nozzle, a suction nozzle tube connected with said attachment means and a nozzle on said tube, valve means for shutting off said suction nozzle tube from said suction duct and means associated with said nozzle holding means controlling said valve means to shut off said suction nozzle tube from said main suction duct when the respective nozzle is held by said holding means.

2. Dental suction apparatus according to claim 1, in which each of said modules having means for attachment of a suction nozzle tube comprises superposed upper, middle and lower casing parts which are sealingly arranged one on top of another and secured together, said suction duct being is said lower casing part.

3. Dental suction apparatus according to claim 2, in which, in each of said modules having means for attachment of a suction nozzle tube, said means for attachment of said suction nozzle tube is on said lower casing part, said nozzle holding means is on said upper casing part and said controlling means is in middle casing part.

4. Dental suction apparatus according to claim 2, in which said valve means comprises a valve seat in said lower casing part and bellows means having an edge clamped between upper and middle casing parts and a lower end portion engageable with said valve seat to close the valve means.

5. Dental suction apparatus according to claim 4, comprising telescopic guide means inside said bellows means for guiding said bellows means in movement toward and away from said valve seat.

6. Dental suction apparatus according to claim 1, comprising switch means for controlling suction producing means connected with said main suction duct and means associated with said nozzle holding means for actuating said switch means when a nozzle is placed on said nozzle holding means.

7. Dental suction apparatus according to claim 1, in which at least one of said modules adjacent a module having means for attachment of a suction nozzle tube comprises a filter chamber interposed between said a suction producing means and said main suction duct, a cover for said filter chamber and a removable and replaceable filter in said chamber.

8. Dental suction apparatus according to claim 1, in which said valve means comprises a valve seat and bellows means expandable to seat on said valve seat to shut off said suction nozzle tube from said main suction duct, said control means comprising means for admitting atmosphere to expand said bellows by differential pressure to seat on said valve seat and thereby close said valve means.

9. Dental suction apparatus according to clalim 8, further comprising a control valve on said nozzle and a control duct extending through said suction nozzle tube from said control valve to said bellows means, said control valve being operable to admit a controlled flow of atmosphere air to said bellows means to control expansion of said bellows means and thereby control the suction applied by said main suction duct to said suction nozzle tube and nozzle.

10. Dental suction apparatus for applying suction comprising a case, a suction duct in said casing, means on said casing for attachment of a suction nozzle tube in communication with said suction duct, a suction nozzle tube and nozzle attached by said attachment means, a filter chamber in said casing, passage means connecting said filter chamber with said suction duct and with said suction nozzle tube, an openable cover for said filter chamber, and a removable filter received in said chamber in such position that air passing from said suction nozzle tube to said suction duct flows through said filter, said filter having handle means for removal of said filter from said filter chamber when said cover is open.

11. Dental suction apparatus according to claim 10, in which said filter is basket-shaped and said handle means comprises a stem extending up from said filter.

12. Dental suction apparatus according to claim 11, in which said filter has a central opening to receive a lower end portion of said stem, said stem having abutments engageable with said opening to retain and position said filter on said stem.

13. Dental suction apparatus according to claim 11, in which said filter chamber has an upwardly-opening opening with a rim and in which a cap on said stem seats on said rim to provide a suction seal for said filter chamber.

14. Dental suction apparatus according to claim 13, in which said stem has abutment means thereon for positioning said cap on said stem, said stem being removable from said cap by downward force on said stem relative to said cap to thereby eject said stem and the filter thereon from said cap.

15. Dental suction apparatus according to claim 11, in which said cover has an opening to receive an upper tip portion of said stem which is thereby visible in said opening to provide a visual indication that a filter is in place in said filter chamber.

16. Dental suction apparatus according to claim 11, in which said filter chamber has an annular shoulder and said filter has a rim which seats on said shoulder to provide a seal.

17. Dental suction apparatus comprising a casing, a main suction duct in said casing, means for attachment of a suction tube to said casing, passage means for connecting said suction tube to said main suction duct including a valve chamber having a valve seat, valve means in said valve chamber for opening and closing said passage means, said valve means comprising a corrugated expansible bellows provided with a sealing lip engageable with said valve seat to close said passage means and thereby cut off suction from said suction tube, and means for controlling the expansion and contraction of said bellows.

18. Dental suction apparatus according to claim 17, in which a control chamber is provided in said casing and the interior of said bellows opens into said chamber.

19. Dental suction apparatus according to claim 18, in which said control means comprises control valve means for admitting atmospheric air into said control chamber and to the interior of the bellows to expand the bellows by differential pressure between the atmosphere and the suction in said main suction duct and thereby close said passage means.

20. Dental suction apparatus according to claim 19, comprising a nozzle on said suction tube and means on said casing for removably holding said nozzle, said control valve means being associated with said nozzle holding means to open said control valve means when said nozzle is held by said nozzle holding means.

21. Dental suction apparatus according to claim 19, comprising a nozzle on said suction tube, regulating valve means on said nozzle and, a control passage extending through said suction tube and to said control chamber, whereby a regulated amount of atmospheric air can be admitted by said regulating valve means and control passage to said control chamber to regulate the expansion of said bellows and thereby regulate the suction applied by said main suction duct to said suction tube.

22. Dental suction apparatus according to claim 17, further comprising telescopic guide means in said bellows to guide said bellows in its expansion and contraction.

23. Dental suction apparatus according to claim 17, in which said control means comprises a bypass suction tube for reducing the pressure inside said bellows to cause said bellows to contract and thereby open said passage means to transmit suction from said main suction duct to said suction tube.

* * * * *